| United States Patent [19] | [11] Patent Number: 4,962,116 |
| Lobbestael et al. | [45] Date of Patent: * Oct. 9, 1990 |

[54] N-(2,6-DISUBSTITUTED AROMATIC)-N'-PYRIDINYL UREAS

[75] Inventors: Sandra J. Lobbestael, Dexter; Ivan C. Nordin, Holland, both of Mich.; Robert Fleming, Milford, Ohio

[73] Assignee: Warner-Lambert Company, Morris Plains, N.J.

[ * ] Notice: The portion of the term of this patent subsequent to Dec. 16, 2003 has been disclaimed.

[21] Appl. No.: 841,503

[22] Filed: Mar. 19, 1986

Related U.S. Application Data

[60] Division of Ser. No. 728,155, Apr. 30, 1985, Pat. No. 4,629,731, which is a continuation of Ser. No. 525,512, Aug. 22, 1983, abandoned.

[51] Int. Cl.$^5$ ............................................. A61K 31/44
[52] U.S. Cl. .................................................... 514/353
[58] Field of Search ......................... 514/353; 546/306

[56] References Cited

U.S. PATENT DOCUMENTS 4,193,788  3/1980  Shudo et al. ............................ 71/94

FOREIGN PATENT DOCUMENTS 2155856  5/1973  France .

Primary Examiner—Jane T. Fan
Attorney, Agent, or Firm—Joan Thierstein

[57] ABSTRACT

N-(2,6-Disubstitutedphenyl)-N'-3- and 4-pyridinyl ureas and pharmaceutically acceptable acid addition salts having anticonvulsant activity are described as well as a process for their manufacture, formulations containing the compounds and a method of treating epilepsy using the compounds in unit dosage form.

1 Claim, No Drawings

N-(2,6-DISUBSTITUTED AROMATIC)-N'-PYRIDINYL UREAS

This application is a divisional of a copending U.S. application Ser. No. 06/728,155 filed Apr. 30, 1985 now U.S. Pat. No. 4,629,731, issued Dec. 16, 1986, which is a continuation of U.S. application Ser. No. 06/525,512 filed Aug. 22, 1983, now abandoned.

BACKGROUND OF THE INVENTION

Despite optimal use of the several antiepileptic drugs marketed in the United States, many patients with epilepsy fail to experience seizure control and others do so only at the expense of significant toxic side effects. In the early 1970's, no convincing evidence had been published that the primary antiepileptic drugs marketed in the U.S. at that time controlled the seizures of more than 50% or improved more than 75% of the patients with epilepsy. The availability and use of several additional drugs since that time has brought improved seizure control to many patients. Notwithstanding the beneficial effects of the current drugs, there is still a need for new antiepileptic drugs with more selective anticonvulsant effects and less toxicity. E. A. Swinyard, et al., Epilepsia, 19, 409 (1978)

Various substituted phenyl pyridinyl ureas have been described but none having anticonvulsant activity. For example, M. I. Bruce and J. A. Zwar in Proc. Roy. Soc. (London), Sec B. 165 (999), 245–65 (1966) disclose many N-mono- and N,N'-disubstituted ureas having cytokinin activity. N-(3,4-dichlorophenyl)-N'-3- and 4-pyridinyl ureas show such activity whereas the corresponding 2,5-dichloro compounds were inactive. In general, the authors concluded that phenyl ring substitution enhanced activity with meta substituents providing highest activity and ortho substituents lowest activity.

German patent publication No. 2,928,485 also describes various ureas including N-(3-chloro-4-trifluoromethylphenyl)-N'-3- and 4-pyridinyl ureas as being useful for inhibiting lipid absorption.

French patent publication No. 2,155,856 teaches various 2-pyridinyl ureas including N-(3,4-dichlorophenyl)-N'-2-pyridinyl urea as having antiinflammatory and analgesic activity The present invention relates to novel 2,6-disubstitutedphenyl 3- and 4-pyridinyl ureas having valuable anticonvulsant properties and are thus useful for treating epilepsy.

SUMMARY OF THE INVENTION

The present invention relates to a compound of the formula

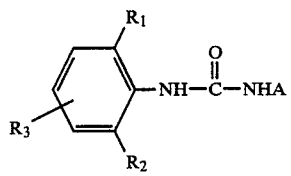

wherein A is 3- or 4-pyridinyl; $R_1$ and $R_2$ are each independently halogen, lower alkyl, lower alkoxy, lower alkanoyl, lower alkoxycarbonyl or nitro, and $R_3$ is hydrogen, halogen, lower alkyl, lower alkoxy, lower alkanoyl, lower alkoxycarbonyl or nitro, or a pharmaceutically acceptable acid addition salt thereof.

The present invention also relates to a process for preparing the compounds of formula I by reacting the appropriate aromatic isocyanate with 3- or 4-aminopyridine.

The present invention further includes a pharmaceutical composition comprising an anticonvulsant effective amount of a compound of formula I together with a pharmaceutically acceptable carrier.

Finally, the instant invention concerns a method for treating epilepsy in mammals suffering therefrom by administering to such mammals an anticonvulsant effective amount of a compound as claimed in claim 1 in unit dosage form.

DETAILED DESCRIPTION OF THE EMBODIMENTS

The term "halogen" as used herein in the definition of the compounds of the formula I includes fluorine, chlorine, bromine, and iodine.

The term "lower" in reference to alkyl, alkoxy, alkanoyl, and alkoxycarbonyl pertains to a straight or branched carbon chain of from 1 to 4 carbon atoms, such as methyl, ethyl, propyl, isopropyl, n-butyl, sec-butyl, iso-butyl, or t-butyl.

The compounds of structural formula I are basic in nature and form pharmaceutically acceptable salts with both organic and inorganic acids. Examples of such acids are acetic, hydrochloric, phosphoric, nitric, sulfuric, fumaric, citric, maleic, malic, and the like The salts are prepared by contacting the free base form of the pyridinyl urea with an equivalent amount of the desired acid in the conventional manner. The free base forms may be regenerated by treating the salt form with a base. For example, dilute aqueous basic solutions may be utilized. Dilute aqueous sodium hydroxide, sodium carbonate or ammonia are suitable for this purpose. The free base forms differ from their respective salt forms somewhat in certain physical properties such as solubility in polar solvents, but the salts are otherwise equivalent to their respective free base forms for purposes of the invention.

The compounds of the invention of formula I can exist in unsolvated as well as solvated forms, including hydrated forms. In general, the solvated forms, with pharmaceutically acceptable solvents such as water, ethanol, and the like are equivalent to the unsolvated forms for purposes of the invention.

A preferred embodiment of the present invention is a compound of the formula I wherein $R_3$ is hydrogen or a pharmaceutically acceptable acid addition salt thereof.

Another preferred embodiment is a compound of the formula I wherein $R_1$ and $R_2$ are each independently halogen or lower alkyl, or a pharmaceutically acceptable acid addition salt thereof Still another preferred embodiment is a compound of the formula I wherein $R_1$ and $R_2$ are each independently chlorine or methyl.

Particular embodiments are the following compounds:
N-(2,6-dichlorophenyl)-N'-4-pyridinyl urea;
N-(2,6-dichlorophenyl)-N'-3-pyridinyl urea;
N-(2,6-dimethylphenyl)-N'-4-pyridinyl urea;
N-(2,6-dimethylphenyl)-N'-3-pyridinyl urea;
N-(2-chloro-6-methylphenyl)-N'-4-pyridinyl urea;
N-(2-chloro-6-methylphenyl)-N'-3-pyridinyl urea;
N-(2,6-diethylphenyl)-N'-4-pyridinyl urea;
N-(2,6-diethylphenyl)-N'-3-pyridinyl urea;

N-(2,6-dimethyl-4-bromophenyl)-N'-4-pyridinyl urea;
N-(2,6-dimethyl-4-bromophenyl)-N'-3-pyridinyl urea;
N-(2,4,6-trimethylphenyl)-N'-3-pyridinyl urea;
N-(2,4,6-trimethylphenyl)-N'-4-pyridinyl urea;
N-(2,4,6-trichlorophenyl)-N'-4-pyridinyl urea;
N-(2,4,6-trichlorophenyl)-N'-3-pyridinyl urea, or a pharmaceutically acceptable acid addition salt thereof.

The compounds of formula I may be prepared by reacting an isocyanate of the formula

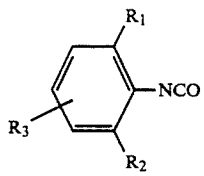

II with an equimolar amount of 3- or 4-aminopyridine in an inert solvent, such as tetrahydrofuran, dioxane, and the like, at elevated temperatures, such as at the boiling point of the solvent used.

The starting materials such as the various isocyanates are known and can be purchased commercially or synthesized by known methods.

The compounds of structural formula I are new chemical substances of value as pharmacological agents for the treatment of convulsions in mammals. The term convulsions is intended to mean the characteristic body movements which are associated with the group of chronic central nervous system disorders termed epilepsies. The anticonvulsant activity of representative compounds of formula I was established by the Maximal Electroshock Seizure Test, MES, a standard test procedure described in E. A. Swinyard, et al., Epilepsia, 19, 409 (1978), which is incorporated herein by reference.

An electroshock apparatus was used to deliver shock via ear clips. Trains of square wave D.C. pulses having a pulse duration of 1 mSec and a frequency of 100 pulses per second were delivered at a current strength of 90 mA for 0.2 seconds. The current strength of 90 mA used in this procedure was approximately four times that required to produce seizures in 99% of mice tested and reliably produces seizure in 100% of control mice.

Mice (five in each group) were tested for the presence of neurotoxicity by determining their ability to cling to an inverted wire mesh screen in 60 seconds (NT test).

In the first test of the anticonvulsant screen, groups of five mice each were given intraperitoneal doses of 30, 100, and 300 mg/kg of representative compounds of the formula I and the mice tested in the MES and NT tests 0.5, 2, and 4 hours later. The number of mice protected in the MES test are shown in the tables as the numerator (a) and the number of mice that fall off the screen in the NT test are shown in the tables as the denominator (b).

| | Anticonvulsant Effect/Ataxia After Intraperitoneal Dosage of Pyridinylureas in Mice | | | | | | | | |
|---|---|---|---|---|---|---|---|---|---|
| | | | | Time after Dose | | | | | |
| | 30 mg/kg Dose | | | 100 mg/kg Dose | | | 300 mg/kg Dose | | |
| R | 0.5 Hr | 2 Hr | 4 Hr | 0.5 Hr | 2 Hr | 4 Hr | 0.5 Hr | 2 Hr | 4 Hr |
| R—(phenyl)—NH—CO—NH—(4-pyridinyl) | | | | | | | | | |
| 2,6-(CH$_3$)$_2$ | 3/0 | 4/0 | 2/1 | 5/3 | 5/0 | 5/1 | 5/5 | 5/5 | 5/5 |
| 2,6-(C$_2$H$_5$)$_2$ | 3/0 | 2/0 | 1/0 | 4/2 | 5/1 | 4/1 | 5/2 | 5/4 | 5/5 |
| 2-Cl-6-CH$_3$ | 4/0 | 1/0 | 3/0 | 5/0 | 5/1 | 5/0 | 5/2 | 5/3 | 5/2 |
| 2,6-Cl$_2$ | 0/0 | 0/0 | 3/0 | 4/0 | 5/0 | 3/1 | 5/0 | 5/2 | 5/2 |
| R—(phenyl)—NH—CO—NH—(3-pyridinyl) | | | | | | | | | |
| 2,6-(CH$_3$)$_2$— | 0/0 | 0/0 | 0/1 | 5/0 | 1/2 | 0/0 | 5/3 | 5/4 | 3/2 |
| 2,6-(C$_2$H$_5$)$_2$— | 0/0 | 0/0 | 0/0 | 3/0 | 0/0 | 0/0 | 5/0 | 4/0 | 0/0 |
| 2-Cl-6-CH$_3$ | 0/0 | 0/0 | 0/0 | 5/0 | 1/0 | 0/1 | 5/2 | 4/1 | 2/0 |
| 2,6-Cl$_2$ | 0/0 | 0/1 | 0/0 | 0/0 | 0/0 | 0/0 | 1/2 | 3/0 | 0/2 |

Legend:
a/b — a = protection against maximal electroshock (out of five tested)
b = fall off the inverted screen (out of five tested)

The compounds of structural formula I can be prepared and administered in a wide variety of oral and parenteral dosage forms.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound of formula I. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e. natural or synthetic gums, resins, methyl cellulose, sodium carboxymethyl cellulose and other well-known suspending agents. Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 100 mg according to the particular application and the potency of the active ingredient.

In therapeutic use as agents for treating convulsions, the compounds utilized in the pharmaceutical method of this invention are administered at the initial dosage of about 0.1 mg to about 21 mg per kilogram daily. A daily dose range of about 0.35 mg to about 12 mg per kilogram is preferred. The dosages, however, may be varied depending upon the requirements of the patient, the severity of the condition being treated and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the preferred methods for preparing the compounds of the invention.

EXAMPLE 1

N-(2,6-Dichlorophenyl)-N'-4-pyridinyl Urea

A solution of 4.7 g (0.05 mole) of 4-aminopyridine in 300 ml of anhydrous tetrahydrofuran was treated with 9.4 g (0.05 mole) of 2,6-dichlorophenylisocyanate. The solution was heated at reflux for 24 hours, cooled, and concentrated in vacuo to a solid. Recrystallization from aqueous ethanol afforded the crystalline product, mp 217°–219° C.

EXAMPLE 2

In a similar manner as described in Example 1, the following compounds were prepared by reacting the appropriate isocyanate with 3- or 4-aminopyridine:

N-(2,6-dichlorophenyl)-N'-3-pyridinyl urea, mp 225°–227° C.;

N-(2,6-dimethylphenyl)-N'-3-pyridinyl urea, mp 190°–192° C.;

N-(2,6-dimethylphenyl)-N'-4-pyridinyl urea, mp 187°–188° C.;

N-(2,6-diethylphenyl)-N'-3-pyridinyl urea, mp 196°–197° C.;

N-(2,6-diethylphenyl)-N'-4-pyridinyl urea, mp 178°–180° C.;

N-(2-chloro-6-methylphenyl)-N'-3-pyridinyl urea, mp 246°–247° C.; and

N-(2-chloro-6-methylphenyl)-N'-4-pyridinyl urea, mp 210°–212° C.

We claim:

1. A method of treating epilepsy in mammals suffering therefrom which comprises administering to such mammal an anticonvulsant effective amount of a compound of the formula

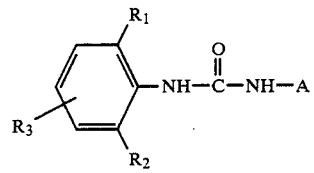

wherein A is 3-pyridinyl; $R_1$ and $R_2$ are independently halogen, lower alkyl, lower alkoxy, lower alkanoyl, lower alkoxycarbonyl or nitro, and $R_3$ is hydrogen, halogen, lower alkyl, lower alkoxy, lower alkanoyl, lower alkoxycarbonyl or nitro, or a pharmaceutically acceptable acid addition salt thereof.

* * * * *